US00PP30864P3

(12) United States Plant Patent
Cerny et al.

(10) Patent No.: US PP30,864 P3
(45) Date of Patent: Sep. 3, 2019

(54) APPLE TREE NAMED 'UEB 41811'

(50) Latin Name: ***Malus domestica* (Borkh.)**
Varietal Denomination: UEB 41811

(71) Applicant: Institute of Experimental Botany AS CR, v.v.i. (UEB), Prague (CZ)

(72) Inventors: Radek Cerny, Ricany u Prahy (CZ); Jan Zima, Turnov (CZ); Otto Louda, Pencin u Liberce (CZ); Jaroslav Tupy, Prague (CZ)

(73) Assignee: Institute of Experimental Botany AS CR, v.v.i. (UEB), Prague (CZ)

( * ) Notice: Subject to any disclaimer, the term of this patent is extended or adjusted under 35 U.S.C. 154(b) by 0 days.

(21) Appl. No.: 15/932,495

(22) Filed: Mar. 7, 2018

(65) Prior Publication Data

US 2018/0263155 P1 Sep. 13, 2018

Related U.S. Application Data

(60) Provisional application No. 62/600,978, filed on Mar. 8, 2017.

(51) Int. Cl.
*A01H 5/08* (2018.01)
*A01H 6/74* (2018.01)

(52) U.S. Cl.
USPC ..... Plt./172
CPC ..... *A01H 6/7418* (2018.05)

(58) Field of Classification Search
USPC ..... Plt./172
See application file for complete search history.

*Primary Examiner* — Susan McCormick Ewoldt
(74) *Attorney, Agent, or Firm* — The Webb Law Firm

(57) ABSTRACT

A new and distinct *Malus domestica* (Borkh.) medium to late ripening, dessert variety that exhibits a columnar tree growth type, $V_f$-resistance against scab, and yellow fruits having a very good taste that are suitable for eating immediately or shortly after harvesting. The new variety is preferable for home apple growing as solitary trees or in groups to function as hedges.

7 Drawing Sheets

Botanical classification: *Malus domestica* (Borkh.).
Varietal denomination: 'UEB 41811'.

BACKGROUND OF THE INVENTION

The present invention comprises a new and distinct cultivar of apple tree botanically classified as *Malus domestica* (Borkh.) and known by the varietal name 'UEB 41811'.

The new variety is the result of a cross in a planned breeding program between 'Gold Bohemia' (female parent, unpatented) and 'Moonlight' (male parent, U.S. Plant Pat. No. 21,511). The cross resulting in 'UEB 41811' occurred in the Spring of 2003 at 310 meters above sea level with a mean annual temperature of 7.7° C. and a mean annual precipitation of 680 mm. The purpose of the breeding program was to develop a medium to late ripening, dessert apple variety having a columnar tree growth type that exhibits $V_f$-resistance against scab. The new variety was discovered in the Fall of 2008 with the first fruiting of the original seedling in the Czech Republic. Subsequently, the new variety was asexually reproduced in Pencin u Liberce in the Czech Republic by budding/grafting on apple rootstocks in the Spring of 2010.

The new variety is similar to its female parent, 'Gold Bohemia', in exhibiting a yellow hue of overcolor and medium to late time of eating maturity. However, 'UEB 41811' exhibits $V_f$-resistance against scab, a columnar tree growth type, and weak tree vigor, while 'Gold Bohemia' exhibits no $V_f$-resistance against scab, a ramified tree growth type, and strong tree vigor. The new variety is similar to its male parent, 'Moonlight', in exhibiting $V_f$-resistance against scab and a columnar tree growth type. However, 'UEB 41811' exhibits a medium to late harvest time and eating maturity shortly after harvesting, while 'Moonlight' exhibits a late harvest time and eating maturity from two months after harvesting in common storage.

Further, when compared to apple tree named 'Tuscan' (U.S. Plant Pat. No. 6,225), both varieties exhibit a columnar tree growth type, fruit bearing mainly on spurs, and medium-sized, similarly shaped fruits with short stems. However, 'UEB 41811' exhibits soft fruit flesh, a greenish fruit flesh color, and $V_f$-resistance against scab, while 'Tuscan' exhibits medium fruit flesh, a white fruit flesh color, and no $V_f$-resistance against scab.

The following characteristics also distinguish the new variety from other varieties known to the breeders:

- Medium to late ripening, dessert-type, diploid variety;
- Columnar tree growth type with a slightly upright, compact, dense growth habit and very short internodes;
- Weak tree vigor;
- Fruit shape is conical;
- Fruit size is medium;
- Fruit ground color is greenish-yellow;
- Small area of light orange-red blush present on some exposed fruits;
- Very good eating qualities; and
- Resistance against scab on $V_f$-gene basis.

The new variety has been trial and field tested and has been found to retain its distinctive characteristics and remain true to type through successive asexual propagations.

DESCRIPTION OF THE DRAWINGS

The accompanying photographic drawings illustrate the new cultivar taken of/from a tree at approximately 7 years of age, except where indicated below, with the color being as nearly true as possible with color illustrations of this type. It should be noted that colors may vary with growing conditions and time of year.

DESCRIPTION OF THE PLANT

Figure 1:
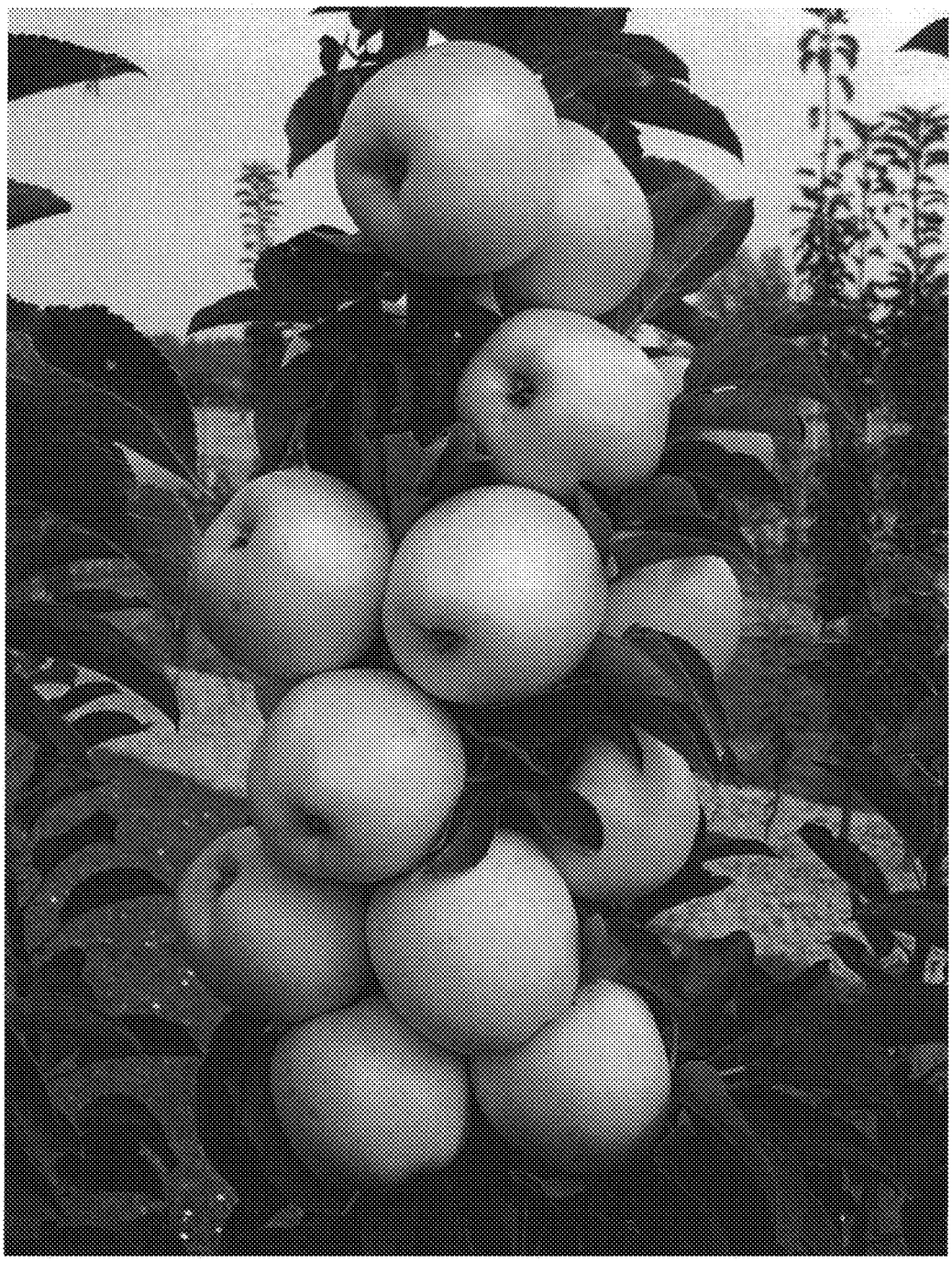
FIG. 1 illustrates a close-up view of fruits of the new variety at picking maturity.
Figure 2:
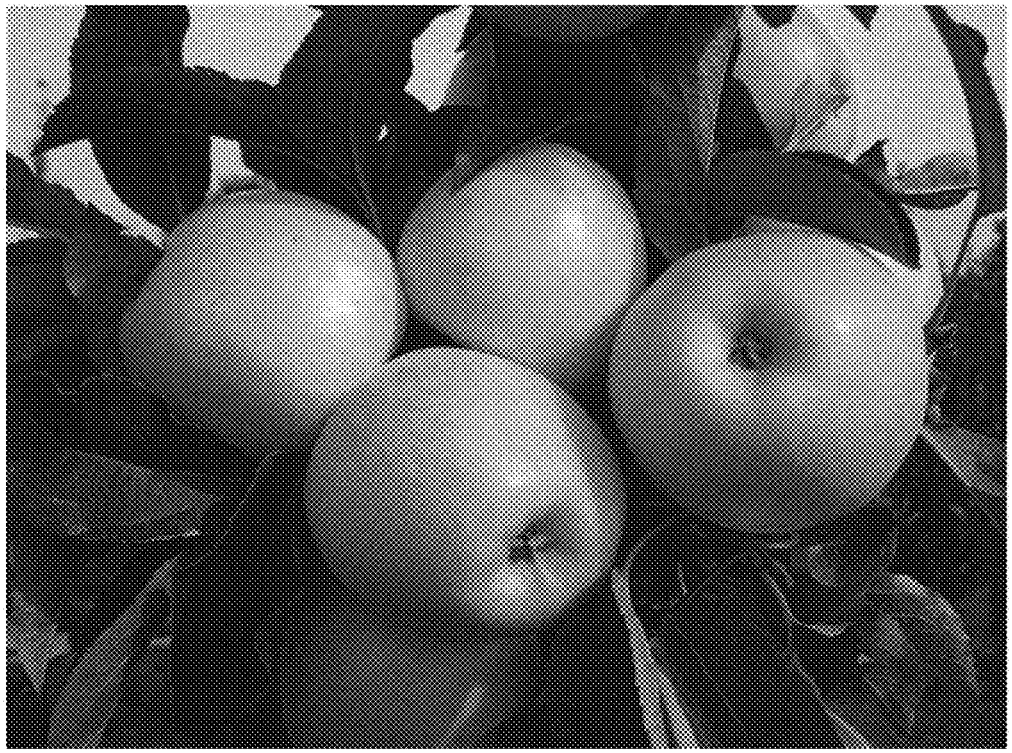
FIG. 2 illustrates details of mature fruits of the new variety.
Figure 3:
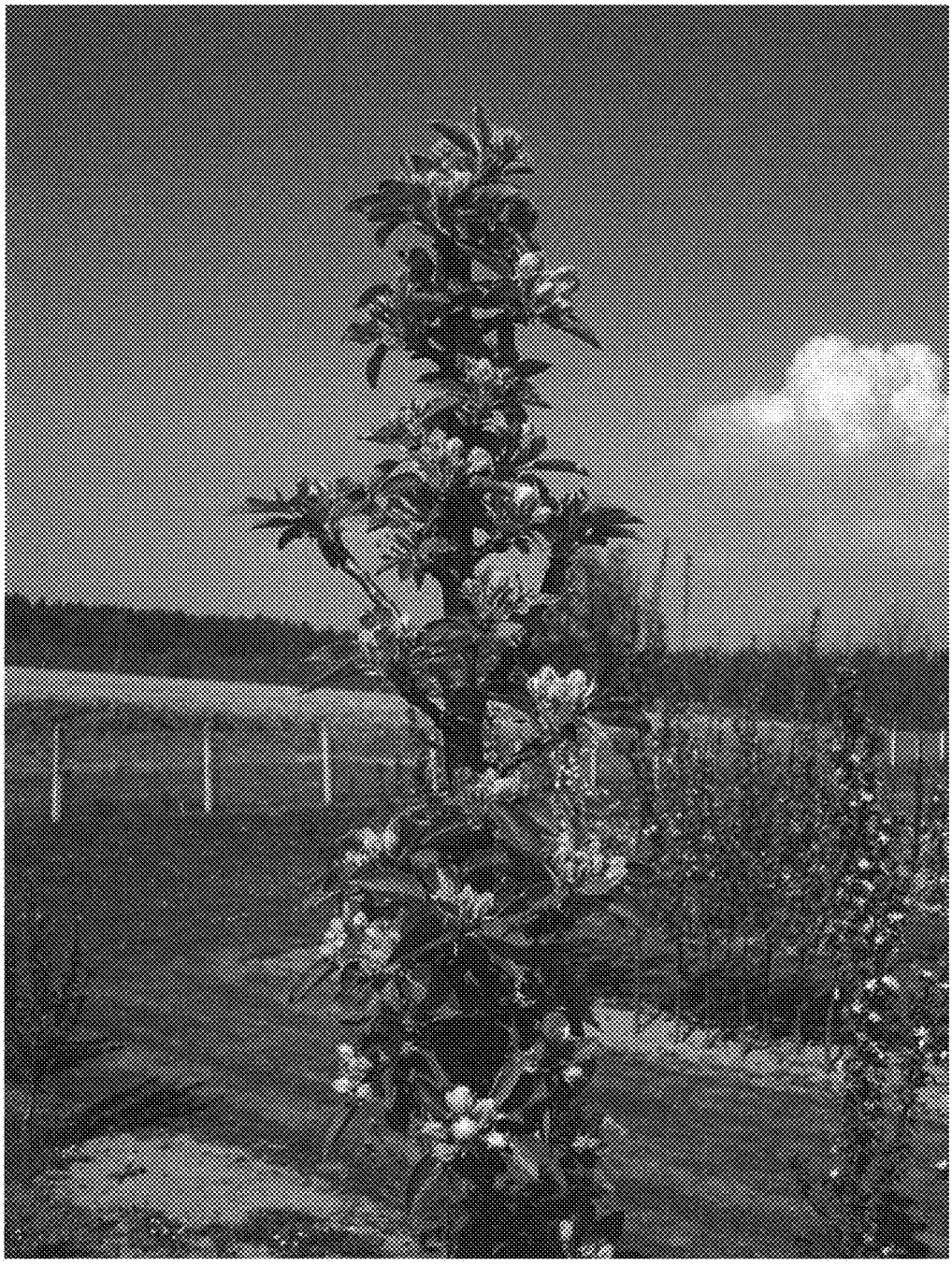
FIG. 3 illustrates the original tree of the new variety, showing its canopy form at blossoming time.
Figure 4:
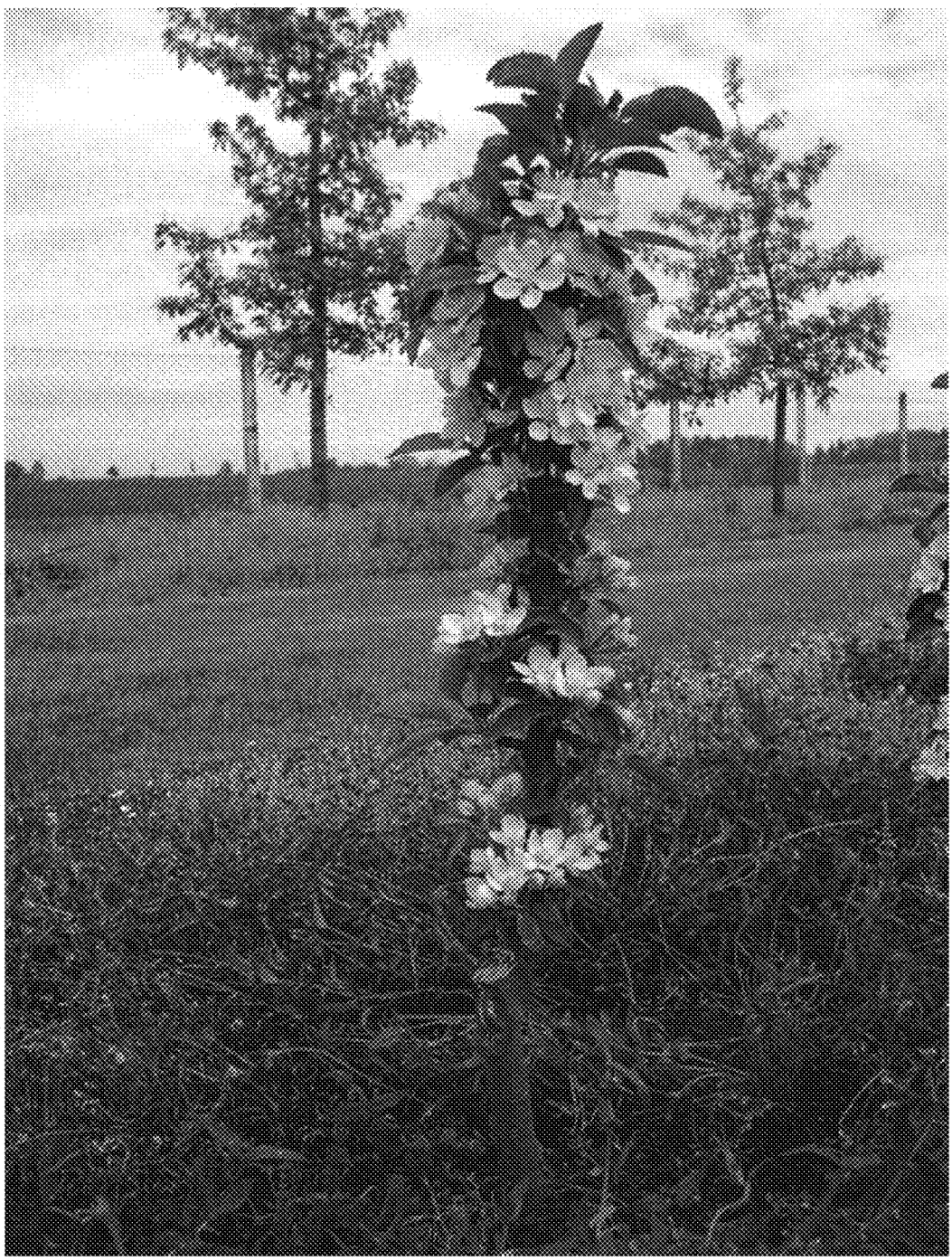
FIG. 4 illustrates a young, flowering tree grafted on MM 106 rootstock after 2 years from grafting.
Figure 5:
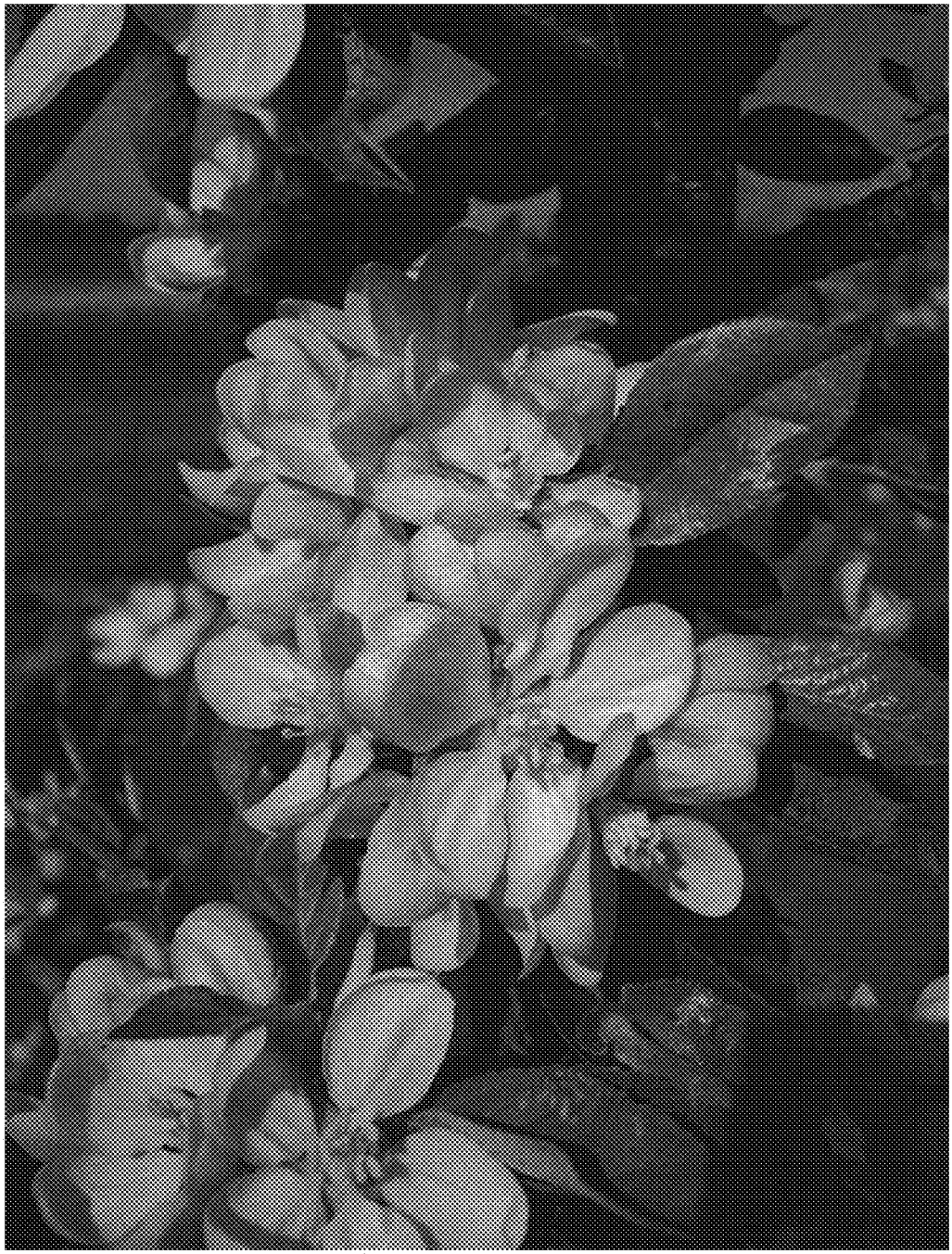
FIG. 5 illustrates blossoms of the new variety.
Figure 6:
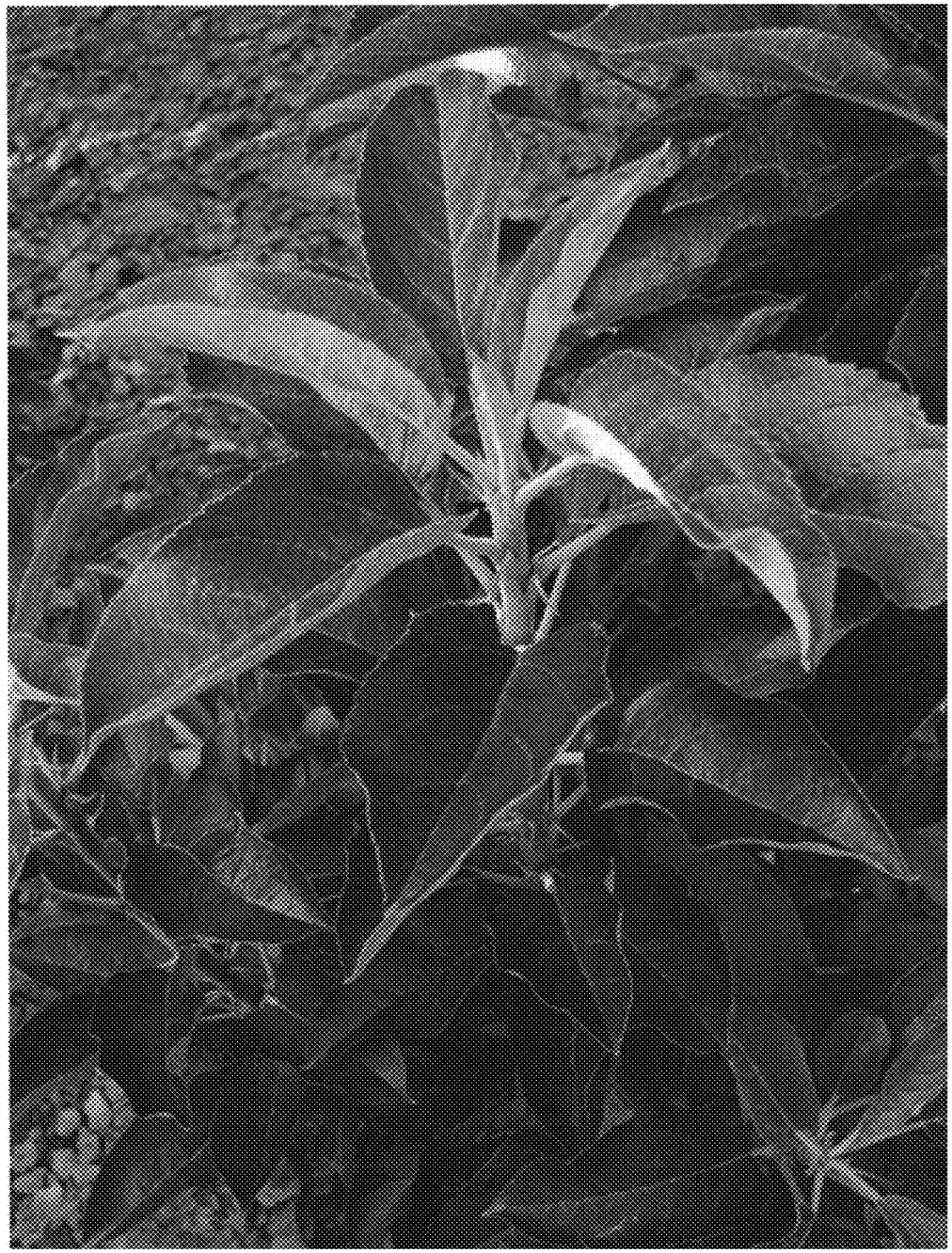
FIG. 6 illustrates a growing shoot of the new variety.
Figure 7:
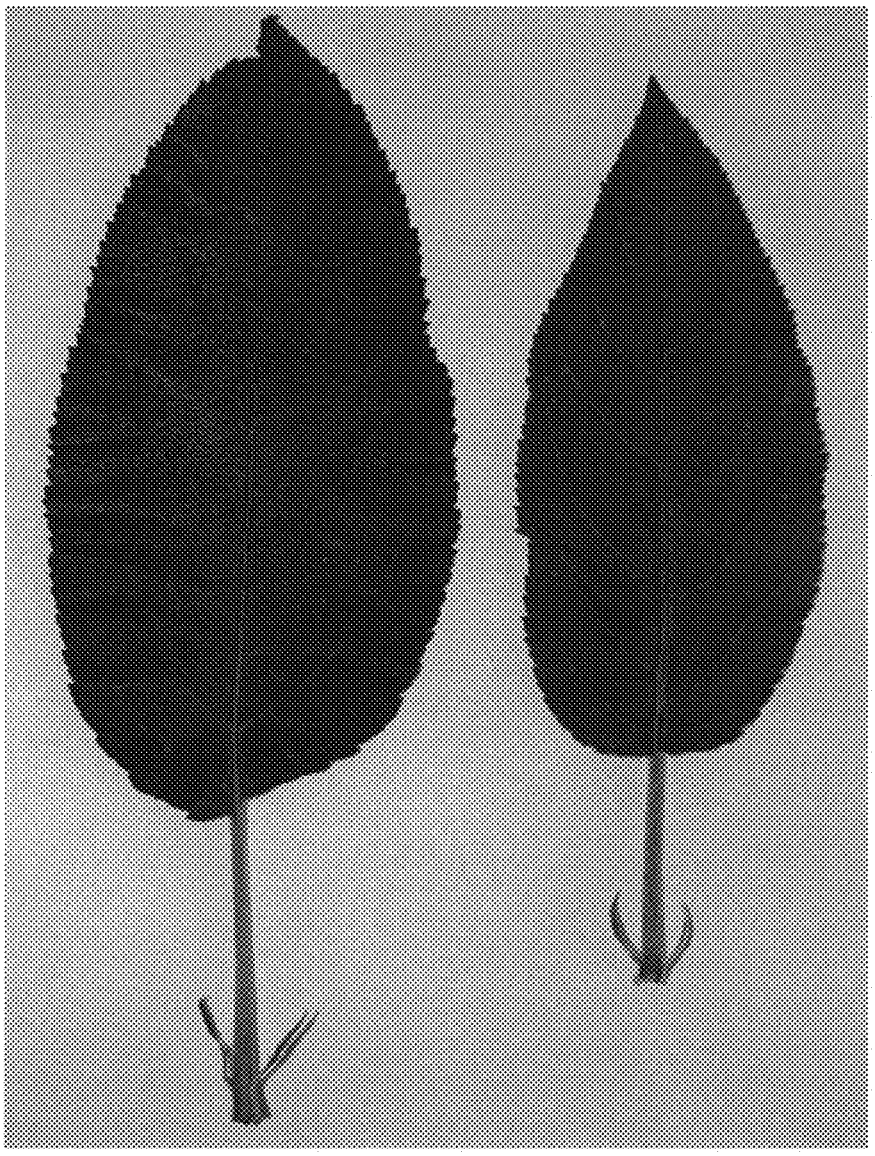
FIG. 7 illustrates a close-up view of a mature leaf and a young leaf of the new variety.

The following detailed description sets forth characteristics of the new cultivar. The new variety was grown under natural field conditions in The Czech Republic. The following fertilizer combination was used (Kg/ha/year): 55 parts nitrogen, 25 parts phosphorous, 60 parts potassium, 55 parts calcium, and 5 parts magnesium. Color references are primarily to The 1986 R.H.S. Colour Chart of The Royal Horticultural Society of London (in association with the Flower Council of Holland), Second Edition, and were identified under natural light.

TREE

Age: Approximately 10 years.
Size: Crown height of 3.2 m, width of 0.7 m.
Vigor: Moderate.
Density: High.
Form: Columnar to pyramidal.
Production: Moderate.
Growth type: Columnar.
Bearing: Annual, on spurs only; slightly alternate.
Average productivity: 5 kg per 5-year old tree (grafted on MM 106 rootstock).

Trunk:
- *Size*.—Approximately 11.0 cm in diameter at 30.0 cm from the soil line.
- *Surface texture*.—Rough and scaly.
- *Bark color*.—Greyed-Orange Group RHS 177B.
- *Lenticels* (150.0 *cm above ground*).—Length: 2.0 mm to 5.0 mm. Width: 0.5 mm to 1.0 mm. Color: Greyed-Orange Group RHS 164B. Density: Variable, with 6 to 8 lenticels on average per 1 $cm^2$.

Branches:
- *Overall description*.—Lacking a conventional branching system along the tree trunk.
- *Diameter*.—Main branches on the trunk are 3.0 to 4.0 cm.
- *Surface texture*.—Rough.
- *Color*.—Greyed-Orange Group RHS 177B.
- *Form*.—Moderate branching.
- *Average crotch angle*.—About 25 degrees.
- *Bud arrangement*.—Alternate. Internode length: 0.6 cm to 1.8 cm.
- *Lenticels* (*on* 1-*year old shoot*).—Length: Typically 2.0 mm to 5.0 mm Width: Typically 0.5 mm to 1.0 mm Shape: Oval. Density: Variable, with 5 to 7 lenticels on average per 1 $cm^2$. Color: Greyed-Orange Group RHS 164B.

Leaves (measured at the middle of growing shoot):
- *Length*.—About 85.0 mm to about 115.0 mm, averaging 98.0 mm.
- *Width*.—About 50.0 mm to about 63.0 mm, averaging about 54.0 mm.
- *Form*.—Predominantly elliptic.
- *Texture*.—Smooth.
- *Thickness*.—Medium.
- *Base*.—Rounded, with variable symmetry.
- *Apex*.—Acute.
- *Margin*.—Biserrate.
- *Pubescence*.—Upper surface: None present. Lower surface: Very fine.
- *Color*.—Young leaves: Upper surface: Yellow-Green Group RHS 144A. Lower surface: Yellow-Green Group RHS 147C. Mature leaves: Upper surface: Green Group RHS 137A to Yellow-Green Group RHS 147A. Lower surface: Close to Green Group RHS 138B.
- *Petiole*.—Shape: Mostly straight, thickened and flattened at the base. Length: About 32.0 mm to 45.0 mm, averaging about 36.0 mm. Diameter: About 2.0 mm to 3.0 mm in the middle. Color: Yellow-Green Group RHS 146D, with some Red-Purple Group RHS 59B near the base.
- *Stipule*.—Length: 1.0 cm. Shape: Elongated, with an acuminate apex. Color: Yellow-Green Group RHS 144A.
- *Veins*.—Venation type: Net-like, medium dense. Color: Upper surface: Yellow-Green Group RHS 144C. Lower surface: Yellow-Green Group RHS 145C.

Flower buds:
- *Pedicel*.—Length: Typically in the range of 16.0 mm to 22.0 mm, with an average of 18.0 mm. Diameter: 1.4 mm on average. Color: Predominantly Yellow-Green Group RHS 144A.
- *Bud*.—Length: 16.0 mm on average. Width: 11.0 mm on average. Color: Red-Purple Group RHS 63A.

Flowers:
- *Bloom timing*.—At the beginning of May (May $6^{th}$, on average) — at the same time as 'Golden Delicious'.
- *Pollination requirements*.—Diploid, self-sterile, needs pollinators such as *Malus* x *zumi* (crab apple) 'Golden Hornet' (unpatented).
- *Number of flowers per cluster*.—5 to 7.
- *Average flower diameter*.—About 43.6 mm (from 38.2 mm to 51.7 mm).
- *Fragrance*.—Faint.
- *Petals*.—Number: 5. Length: From 18.0 mm to 22.0 mm, with an average of 20.0 mm. Width: From 12.0 mm to 16.0 mm, with an average of 14.0 mm. Shape: Ovate. Apex: Obtuse. Base: Rounded. Aspect: Positioned touching to overlapping. Margin: Entire. Texture and appearance: Soft and smooth. Color: When opening: Upper surface: White Group RHS 155C and Red-Purple Group RHS 65B to 65C. Lower surface: White Group RHS 155C and Red-Purple Group RHS 65A to 65B. Fully opened: Upper surface: White Group RHS 155C and Red-Purple Group RHS 65A to 65B. Lower surface: White Group RHS 155B and Red-Purple Group RHS 63C to 63D.

*Sepals*.—Number: 5 (average). Shape: Long-conical; pointed. Margin: Entire. Texture: Finely pubescent. Length: 10.0 mm to 12.0 mm from the union. Width: 4.0 mm at the base, 2.5 mm in the middle. Color: Upper surface: Yellow-Green Group RHS 144A, with a Red-Purple Group RHS 59B apex. Lower surface: Yellow-Green Group RHS 146C, with a Red-Purple Group RHS 59B apex.

*Stamens*.—Number (per flower): 20. Filament length: 7.0 mm to 10.0 mm.

*Anthers*.—Shape: Oval. Length: 2.0 mm to 3.0 mm Color: Yellow Group RHS 10B.

*Pollen*.—Color: Yellow Group RHS 13C. Amount (generally): Medium to high.

*Pistils*.—Length: 16.0 mm on average.

*Style*.—Length: 11.0 mm on average. Color: Yellow-Green Group RHS 144A to 144B.

*Stigma*.—Shape: Rounded. Color: Yellow-Green Group RHS 151A.

Fruit:

*Maturity when described*.—Eating maturity after two months in common storage.

*Date of picking*.—October of 2017.

*Size*.—Axial diameter: Average of 67.0 mm. Transverse diameter: Average of 76.0 mm.

*Weight per fruit*.—Average of 172 g (from 129 g to 212 g).

*Form*.—Conical.

*Cavity*.—Description: Funnel-shaped, free of russet. Depth: Average of 16.0 mm. Breadth: Average of 33.0 mm.

*Basin*.—Description: Funnel-shaped, smooth, with weak and irregular ribbing. Depth: Average of 11.0 mm. Width: Average of 23.0 mm.

*Calyx*.—Persistent with semi-erect lobes.

Skin:

*Thickness*.—Thin to medium.

*Texture*.—Smooth, free of russet.

*Tendency to crack*.—Absent.

*Color*.—Yellow-Orange Group RHS 22B, with a small area of light orange-red blush present on some exposed fruits.

*Ground color*.—Yellow Group RHS 3A, with very few, small lenticels present.

Flesh:

*Aroma*.—Strong.

*Color*.—Yellow Group RHS 4C.

*Texture*.—Finely grained, medium firmness, and crisp.

*Eating quality*.—Very good, rich, with a harmonic sugar to acid ratio.

Core:

*Bundle area*.—On longitudinal section defined with moderately distinct vascular strands as heart-shaped having a width of 37.0 mm and a height of 34.0 mm; moderately open locules.

*Calyx tube*.—Narrow and funnel-shaped.

*Depth of tube to shoulder*.—12.0 mm.

*Styles*.—Persistent as dry residues.

*Stamens*.—Persistent as dry residues.

*Seed cells*.—Wall: Smooth. Depth: 11.0 mm. Breadth: 7.0 mm on cross section. Longitudinal section: About 21.0 mm (length of seed cell).

Seeds:

*Number perfect*.—10.

*Number in one cell*.—2.

*Length*.—8.0 mm.

*Breadth*.—4.0 mm.

*Form*.—Long conical with an acute tip.

*Color*.—Greyed-Orange Group RHS 166A.

Stem:

*Length*.—18.0 mm on average (typically 10.0 mm to 22.0 mm).

*Width*.—2.5 mm on average.

*Color*.—Yellow-Green Group RHS 152B.

Use: As a medium to late ripening, dessert apple variety having a columnar tree growth type with fruits of very good eating quality and maturity directly after picking that is preferable for home apple growing.

Shipping quality: Average.

Keeping quality: Average — skin tends to shrink after two months in common storage.

Tree winter hardiness: No frost damage observed at the place of origin, lowest winter temperatures approximately −20° C.

Bud winter hardiness: No frost damage observed at the place of origin, lowest winter temperatures approximately −20° C.

Drought tolerance: Unknown.

Disease resistance: $V_f$-resistance against scab.

We claim:

1. A new and distinct variety of *Malus domestica* (Borkh.) apple tree plant substantially as is herein described and illustrated.

* * * * *